United States Patent
Ames et al.

(10) Patent No.: US 11,439,619 B2
(45) Date of Patent: *Sep. 13, 2022

(54) PHOSPHAPLATIN COMPOUNDS AS IMMUNO-MODULATORY AGENTS AND THERAPEUTIC USES THEREOF

(71) Applicant: Phosplatin Therapeutics Inc., New York, NY (US)

(72) Inventors: Tyler Ames, Brooklyn, NY (US); Matthew Price, New York, NY (US)

(73) Assignee: Phosplatin Therapeutics Inc., New York, NY (US)

( * ) Notice: Subject to any disclaimer, the term of this patent is extended or adjusted under 35 U.S.C. 154(b) by 39 days.

This patent is subject to a terminal disclaimer.

(21) Appl. No.: 16/645,043

(22) PCT Filed: Sep. 7, 2018

(86) PCT No.: PCT/US2018/049980
§ 371 (c)(1),
(2) Date: Mar. 6, 2020

(87) PCT Pub. No.: WO2019/051246
PCT Pub. Date: Mar. 14, 2019

(65) Prior Publication Data
US 2021/0121434 A1    Apr. 29, 2021

Related U.S. Application Data

(60) Provisional application No. 62/555,676, filed on Sep. 8, 2017.

(51) Int. Cl.
*A61K 31/282* (2006.01)
*A61P 35/00* (2006.01)
*A61K 45/06* (2006.01)

(52) U.S. Cl.
CPC ............ *A61K 31/282* (2013.01); *A61K 45/06* (2013.01); *A61P 35/00* (2018.01)

(58) Field of Classification Search
None
See application file for complete search history.

(56) References Cited

U.S. PATENT DOCUMENTS

| 8,653,132 | B2 | 2/2014 | Bose |
| 9,688,709 | B2 | 6/2017 | Bose |
| 10,668,080 | B2* | 6/2020 | Price ................. A61P 35/04 |
| 2013/0064831 | A1 | 3/2013 | Humphrey |
| 2017/0224711 | A1 | 8/2017 | Bose |

FOREIGN PATENT DOCUMENTS

| JP | 2013529219 A | 7/2013 |
| JP | 2015519372 A | 7/2015 |
| JP | 2017515859 A | 6/2017 |
| JP | 7023968 B2 | 2/2022 |
| TW | 201828947 A | 8/2018 |
| WO | 2011153365 A1 | 12/2011 |
| WO | 2013181452 A1 | 12/2013 |
| WO | 2015176033 A1 | 11/2015 |
| WO | 2017/129790 A1 | 8/2017 |

OTHER PUBLICATIONS

Iwata et al., Pios One (May 30, 2017), 12(5), pp. e0178221-e0178221/13.*
Bose et al., Journal of Medicinal Chemistry (2015), 58(21), pp. 8387-8401.*
Tesniere A et al: "Immunogenic death of colon cancer cells treated with oxaliplatin", Oncogene, Nature Publishing Group, United Kingdom, vol. 29, No. 4, Jan. 28, 2010 (Jan. 28, 2010), pp. 482-491.
Yamazaki Takahiro et al: "PT-112 induces immunogenic cell death and synergizes with immune checkpoint blockers in mouse tumor models", Oncoimmunology, vol. 9, No. 1, Jan. 1, 2020 (Jan. 1, 2020), p. 1721810.
European Search Report dated Apr. 30, 2021, for related European Application No. 18852857.4, 9 pages.
Pfirschke C, et al. "Immunogenic chemotherapy sensitizes tumors to checkpoint blockade therapy", Immunity, Feb. 16, 2016; 44(2):343-54, 27 pages.
Taiwan Office Action and Search Report dated Jun. 14, 2022 in Taiwan Patent Application No. 107131765, 7 pages.
Bose et al., "Non-DNA-binding platinum anticancer agents: Cytotoxic activities of platinum-phosphato complexes towards human ovarian cancer cells", PNAS, vol. 105, No. 47, Nov. 25, 2008, pp. 18314-18319.

* cited by examiner

Primary Examiner — Brian J Davis
(74) Attorney, Agent, or Firm — Fox Rothschild LLP (57) ABSTRACT

Use of (pyrophosphato)platinum(II) or platinum(IV) complexes ("phosphaplatins"), especially 1,2-cyclohexanediamine(pyrophosphato) platinum(II), as immunogenic cell death (ICD) inducing agents and their combination with immune checkpoint protein inhibitors for treatment of cancers, and the mechanistic rationale for the methods thereof, are disclosed.

19 Claims, 7 Drawing Sheets

PHOSPHAPLATIN COMPOUNDS AS IMMUNO-MODULATORY AGENTS AND THERAPEUTIC USES THEREOF

CROSS REFERENCE TO RELATED APPLICATIONS

This application is the U.S. national phase application of International Application No. PCT/US2018/049980, filed on Sep. 7, 2018, which claims the benefit under 35 U.S.C. § 119(e) of U.S. Provisional Application No. 62/555,676 filed on Sep. 8, 2017, both of which are incorporated herein by reference in their entirety.

TECHNICAL FIELD OF THE INVENTION

This invention relates to use of phosphaplatin compounds as therapeutic agents for the treatment of cancer and methods thereof, in particular regarding their immuno-modulatory mechanism of action that can result in combination synergy.

BACKGROUND OF THE INVENTION

Platinum-based antineoplastic agents, often referred to simply as platins, are a class of compounds used to treat a broad range of different types of cancers. As the name indicates, platin agents all contain a platinum atom in their structure. The clinical use of these agents is dominated by three compounds: cisplatin, carboplatin, and oxaliplatin. These agents all share several features, including a mechanism of action that is thought to be centered around the binding and damaging of nuclear DNA, resulting in transcriptional interference and apoptosis.

Despite being used in the clinic since the 1970s, these agents have remained relevant in the modern era of cancer treatment, being used mostly in combination with other cytotoxic and targeted agents. However, they are not without their problems. Specifically, they can cause substantial toxicities involving several organs and body systems, including but not limited to the kidneys, blood, and peripheral nervous system. This can cause reductions in the quality of life of patients on these therapies, as well as dose reductions and premature treatment discontinuations.

Outside of issues involving tolerability, during and after treatment drug resistance can emerge, including from the upregulation of DNA repair pathways, making continued or subsequent treatment with these agents unproductive. This is a particularly problematic issue, given the wide-spread use of these agents.

Additionally, with immuno-oncology (I-O) agents, in particular checkpoint inhibitors (CPIs), being used and approved in more cancer indications, it is becoming apparent that these CPIs only generate responses in a minority of patients. The research field has determined this is in part due to the CPIs inability on their own to recruit immune T cells to the tumor microenviroment. Novel agents are needed that a) can be used in conjunction with CPIs to improve responses rates, which in many indications are quite low, and b) can be used to treat the emerging category of CPI resistant or refractory patients. In order for such a combination to be successful, the research field recognizes priorities that such combination agents have an excellent tolerability profile and are capable of engendering immuno-modulatory responses such as immunogenic cell death (ICD).

Phosphaplatins, previously discovered agents that derive their anti-cancer activity independently of DNA damage and repair pathways, and cause limited to no renal or neurotoxicity in animal models, represent an opportunity to overcome the limitations associated with conventional platins, as cited above. We disclose herein our discovery of the immuno-modulatory mechanism of ICD generated by phosphaplatins, and the anti-cancer therapeutic uses thereof.

SUMMARY OF THE INVENTION

A new class of platinum-based antitumor agents were disclosed in U.S. Pat. Nos. 7,700,649 and 8,034,964 (inter alia), both to R. Bose. Named phosphaplatin complexes, since the platinum atom is conjugated to a pyrophosphate group, these agents operate differently from cisplatin, carboplatin, and oxaliplatin, as their mechanism of action does not center around the binding and damaging of nuclear DNA. This allows these agents to be active in patients who have become resistant to previous platinum therapy. Additionally, the mechanism involves the induction of a rare form of apoptosis known as immunogenic cell death (ICD), which induces an adaptive immune response to the cancer and creates a rationale for combinations with the emerging class of immune checkpoint inhibitors and other I-O agents.

The method comprises, or consists essentially of, administering to a subject having a cancer a therapeutically effective amount of a compound according to any one of formulae I to IV:

or a pharmaceutically acceptable salt or composition thereof, to induce immunogenic cell death in the subject, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

In some preferred embodiments, the phosphaplatin compound is 1,2-cyclohexanediamine-(dihydrogen pyrophosphato)platinum(II) ("pyrodach-2") having a structure of formula selected from the group consisting of:

(R,R)-pyrodach-2

(S,S)-pyrodach-2 cis-pyrodach-2 which are, respectively, trans-(R,R)-1,2-cyclohexanediamine(pyrophosphato) platinum(II) ("(R,R)-pyrodach-2" or "PT-112"), trans-(S,S)-1,2-cyclohexanediamine(pyrophosphato) platinum(II) ("(S,S)-pyrodach-2"), and cis-1,2-cyclohexanediamine (pyrophosphato) platinum(II) ("cis-pyrodach-2").

In some more preferred embodiments, the phosphaplatin compound is administered to a subject as an ICD inducing agent in conjunction with an immune checkpoint protein inhibitor.

Other aspects and advantages of the invention will be better appreciated in view of the following drawings, description, and claims.

DETAILED DESCRIPTION OF THE INVENTION

The present invention is based on the surprising discovery that phosphaplatin complexes potently induce immunogenic cell death and subsequent immune T cell recruitment to the tumor microenvironment, a mechanistic property distinct from other Pt-containing compounds that has implications on their use alone or in combination with other agents within oncology and hematology.

In one aspect, the present invention provides a method of treating cancer in a subject, comprising administering to the subject a therapeutically effective amount of a phosphaplatin compound having a structure of formula I or II:

or a pharmaceutically acceptable salt thereof, to induce immunogenic cell death in the subject, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

The cancer can be selected from colon cancer, pancreatic cancer, gastric cancer, liver cancer, breast cancer, prostate cancer, lung cancer, bladder cancer, urothelial carcinoma, thymic epithelial tumors, head and neck cancer, and skin cancers, such as basal cell carcinoma and melanomas.

In some embodiments, the cancer can be selected from osteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JMML), myelodysplastic syndromes, myelofibrosis, myeloproliferative neoplasms, polycythaemia vera, and thrombocythaemia, or the like.

In some further embodiments, the cancer is selected from osteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma, leukemia, or the like. In one preferred embodiment, the bone or blood cancer is multiple myeloma.

In one embodiment of this aspect, $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

In another embodiment of this aspect, the phosphaplatin compound is selected from the group consisting of pharmaceutically acceptable salts, and mixtures thereof.

In a preferred embodiment, the phosphaplatin compound is R,R-pyrodach-2 having the formula:

In one aspect, the present invention provides a method for treating a subject having a cancer, comprising administering to the subject a therapeutically effective amount of a phosphaplatin compound having a structure of formula III or IV:

or a pharmaceutically acceptable salt thereof, to induce immunogenic cell death in the subject, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

In one embodiment of this aspect, $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

In another embodiment of this aspect, the phosphaplatin compound has a formula (IV), wherein $R^3$ is 1,2-ethylenediamine or cyclohexane-1,2-diamine.

In some embodiments, the administering comprises intravenous or intraperitoneal injection.

In some embodiments, the administering comprises intravenous injection.

In some embodiments, the administering comprises intraperitoneal injection.

In some embodiments, the method is used in conjunction with administering to the subject a second anticancer agent.

In some embodiments, the second anticancer agent is selected from the group consisting of alkylating agents, glucocorticoids, immunomodulatory drugs (IMiDs) and proteasome inhibitors.

In some embodiments, the second anti-cancer agent is selected from the group consisting of cyclocreatine, a RNAi agent, a nucleic acid, a vector, 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS), Robatumumab, and IGF1-R Inhibitors.

In another aspect, the present invention provides a method for treating a subject having cancer, comprising administering to the subject a therapeutically effective amount of a phosphaplatin compound having a structure of formula I or II:

pharmaceutically acceptable salts, and mixtures thereof.

In a preferred embodiment, the phosphaplatin compound is R,R-pyrodach-2 (PT-112) having the formula:

In another aspect, the present invention provides a method for treating a subject having cancer, comprising administering to the subject a therapeutically effective amount of a phosphaplatin compound having a structure of formula III or IV:

(I)

(II)

(III)

(IV)

or a pharmaceutically acceptable salt thereof, as an ICD-inducing agent in conjunction with an immune checkpoint protein inhibitor, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

In some embodiments of this aspect, $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

In some embodiments of this aspect, the phosphaplatin compound is selected from the group consisting of:

or a pharmaceutically acceptable salt thereof, as an ICD-inducing agent in conjunction with an immune checkpoint protein inhibitor, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

In some embodiments of this aspect, $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

In some embodiments of this aspect, the monomeric platinum (IV) pyrophosphate complex has a formula (IV), wherein $R^3$ is 1,2-ethylene-diamine or cyclohexane-1,2-diamine.

In some embodiments of this or the previous aspect, the phosphaplatin (IV) or (II) compound is administered to the subject at a certain time prior to administration of the immune checkpoint protein inhibitor.

In some embodiments of this or the previous aspect, the phosphaplatin (IV) or (II) compound is administered to the subject at substantially the same time as administration of the immune checkpoint protein inhibitor.

In some embodiments of this or the previous aspect, the phosphaplatin (IV) or (II) compound is administered to the subject at a certain time after administration of the immune checkpoint protein inhibitor.

In some embodiments of this or the previous aspect, the subject is a patient having a cancer having low or no response to treatment with a previous immune checkpoint inhibitor treatment.

In some embodiments of this or the previous aspect, the immune checkpoint inhibitor is selected from the group consisting of PD-1 inhibitors, PD-L1 inhibitors, B7-1/B7-2 inhibitors, CTLA-4 inhibitors, or the like, and combinations thereof.

In some embodiments of this or the previous aspect, the immune checkpoint protein inhibitor is an antibody selected from the group consisting of Pembrolizumab (Keytruda), Nivolumab (Opdivo), Pidilizumab (CT-011), Atezolizumab (Tecentriq), Avelumab (Bavencio), Durvalumab (Imfinzi), Ipilimumab (Yervoy), or the like, and combinations thereof.

In some embodiments of this or the previous aspect, the administering comprises intravenous or intraperitoneal injection.

In some embodiments of this or the previous aspect, the cancer is selected from the group consisting of colon cancer, pancreatic cancer, gastric cancer, liver cancer, breast cancer, prostate cancer, lung cancer, bladder cancer, urothelial carcinoma, thymic epithelial tumors, head and neck cancer, skin cancers, such as basal cell carcinoma and melanomas, osteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JMML), myelodysplastic syndromes, myelofibrosis, myeloproliferative neoplasms, polycythaemia vera, thrombocythaemiaosteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma and leukemia.

In some embodiments of this or the previous aspect, sometimes preferably, the cancer is characterized with a low level of tumor-infiltrating lymphocytes (TILs).

In another aspect, the present invention is directed to use of any one of the pyrophosphate platinum (II) or platinum (IV) complexes disclosed herein in conjunction with an immune checkpoint protein inhibitor, whether or not disclosed herein, in the manufacture of medicament(s) for treatment of a cancer. The cancer can be any of the cancers, disclosed or not disclosed herein, responsive to treatment with such medicament(s).

In a preferred embodiment, the pyrophosphate platinum (II) complex is PT-112.

As a person of skill in the art would understand, the present invention encompasses any reasonable combinations of the illustrated embodiments disclosed herein, which would provide a beneficial effect to a cancer patient.

The terminology used in the description of the invention herein is for describing particular embodiments only and is not intended to be limiting of the invention. As used herein, the singular forms "a," "an," and "the" are intended to include the plural forms as well, and vice versa, unless the context clearly indicates otherwise.

The term "about," as used herein, is intended to mean up to ±10% of an indicated value. Any ranges mentioned in the specification or the claims are to be understood as including the range itself and also anything subsumed therein, including both endpoints.

The term "subject," as used herein, generally refers to a mammalian animal, including humans and animals such as dogs, cats, horses, and so on.

The term "aliphatic amine," as used herein, refers to an amine compound in which the nitrogen atom of an amino group is connected to an aliphatic group, not an aromatic ring, for example, methylamine, butylamine, ethylene diamines, cyclohexylamine, cyclohexane-diamines, or the like. The term "aliphatic diamine," as used herein, refers to a subset of aliphatic amine compounds which contain two amino groups.

The term "aromatic amine," as used herein, refers to an amine compound in which the nitrogen atom of an amino group is connected to an aromatic ring, for example, aniline, phenylene diamines, or the like, or refers to a heterocyclic amine, such as pyridine, or the like. The term "aromatic diamine," as used herein, refers to a subset of aromatic amine compounds which contain two amino groups.

The term "substituted" or "optionally substituted," as used herein in association with an aliphatic or aromatic amine, refers to that the aliphatic or aromatic group can be optionally substituted by one to five, preferably one to three, substituents independently selected from the group consisting of halogen, —CN, nitro, $C_{1-4}$alkyl, $C_{1-4}$haloalkyl, $C_{3-6}$ cycloalkyl, —O—$C_{1-4}$haloalkyl, and —O—$C_{1-4}$ alkyl. In some embodiments, sometimes preferably, the aliphatic and aromatic amines are unsubstituted.

The term "composition," "pharmaceutical composition," or "pharmaceutically acceptable composition" means that a composition comprising a phosphaplatin compound and at least one pharmaceutically acceptable ingredient selected from carriers, diluents, adjuvants, and vehicles, which, as known in the art, generally refer to inert, non-toxic, solid or liquid fillers, diluents, or encapsulating materials unreactive with the phosphaplatin complexes.

The phosphaplatin compounds, pharmaceutical salts or complexes thereof, can be administered in a variety of ways, for example, orally, subcutaneously or parenterally including intravenous, intraarterial, intramuscular, intraperitoneally, intratonsillar, and intranasal administration as well as intrathecal and infusion techniques. A pharmacological formulation comprising the phosphaplatins containing any compatible carrier, such as various vehicles, adjuvants, additives, and diluents can be administered to the patient in an injectable formulation. When administered parenterally, they generally will be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, or the like), suitable mixtures thereof, and vegetable oils. Sterile injectable solutions can be prepared by incorporating the phosphaplatin complexes in the required amount of the appropriate solvent with one or more of the other ingredients, as desired.

The disclosure is intended to cover any dosage of the phosphaplatin compounds that can cause therapeutic benefits on a subject having any cancer, although the range of 1 to 200 mg/Kg based on a subject's body weight is disclosed to be generally preferred. The compound R,R-pyrodach-2 (PT-112) has been used in a safe human dosing range from 12 to 420 mg/m$^2$ based on body surface area.

In some embodiments, the method of the present invention may be preferably used in conjunction with other therapies, for example, stem cell transplantation, chemotherapy along with other anticancer drugs, and/or radiation therapy.

EXAMPLES

The following non-limiting examples further illustrate certain aspects of the present invention.

PT-112 is a new chemical entity under clinical development in the US and the People's Republic of China, designed to minimize particular toxicities associated with traditional platinum agents and drug resistance stemming from DNA damage and repair. As a pyrophosphate-conjugated Pt-containing anti-neoplastic therapeutic, PT-112 differs from platinum therapies in both mechanism and toxicity. In previous work in cancer cell models, PT-112 exposure resulted in significantly less Pt accumulation in both DNA and whole cell extracts compared with exposure to either cisplatin (cis) or oxaliplatin (oxali). Nonetheless, PT-112 has potent cytotoxic activity in in vitro systems, implying a different spectrum of targets for PT-112 in comparison to traditional platinum compounds. We explored the activity and mechanism of action of PT-112 by investigating impacts on cancer related proteins and pathways, including those connected to immunogenic cell death (ICD), as well as how PT-112 potency is affected by DNA repair pathways. In addition, PT-112 anticancer activity, pharmacokinetics (PK), and toxicity were measured in multiple in vivo systems.

In vitro experiments revealed unique features of PT-112 in both activity and mechanism. Specifically, IC$_{50}$ values for PT-112 were superior to cis, carboplatin (carbo), and oxali in a majority of cell lines, in a broadly platinum-resistant cell panel. A high degree of correlation was observed between cis and carbo activity, but not between those agents and PT-112. A correlation between PT-112 and oxali was also observed, which led to investigation of cellular targets and mechanisms not shared by these two agents. In an HCT116 colon cancer model, PT-112 had a minimal effect on the phosphorylation of H2AX and on induction of Ku70 versus oxali at equipotent concentrations, implying that PT-112 has a low degree of reliance on DNA-binding and damage for anti-cancer activity. Additionally, PT-112's potency did not differ significantly between nucleotide excision repair (NER)-deficient HCT116 cells and their isogenic NER-proficient counterparts. Conversely, NER-competent cells were less sensitive then the NER-deficient cell line to cis treatment. PT-112 also had a noteworthy impact on p53 and MDM2 levels, in addition to numerous proteins involved in inhibition of cell cycle progression at the G1/S phase, such as p16 and p21 and downstream members of the CDK and E2F families. PT-112 also induced a variety of effects indicative of ICD induction at a significantly greater extent than oxali, which is considered a bona fide ICD-inducing agent. These effects comprise the release of HMGB1 and ATP, the cell surface exposure of calreticulin (CRT), and the suppression of STATS.

In vivo experiments demonstrated the activity of PT-112 as a single agent across multiple tumor models, as well as pronounced differences in pharmacokinetics and toxicity relative to other platinum compounds. Specifically, in the GXF97 gastric patient-derived xenograft (PDX) model, a durable response was observed (minimum $\Delta T/\Delta C=2.5\%$) at 90 mg/kg. Cases of complete response were observed, albeit at higher doses not tolerated by all other mice in those cohorts (data not shown). Sustained tumor growth delay was observed with PT-112 treatment in the CXF280 colon PDX and PANC1 pancreatic cancer models.

PK experiments in rats demonstrated a large fraction of PT-112-derived Pt in the plasma ultrafiltrate (PUF) relative to total plasma Pt (72.8%), notably contrasting with data from the literature using oxali, where a much smaller fraction of Pt in the PUF was observed (28.2%). Importantly, Pt in plasma, but not present in the PUF, is believed to be protein-bound and not bioavailable for therapeutic benefit. An LC-MS/MS analytical method developed to detect parent PT-112 also revealed its predominance, indicating stability of PT-112 in plasma.

Rats tolerated 7-fold higher concentrations of PT-112 with minimal effects on renal function (creatinine, BUN and GFR) than that of cis, which caused morbidity. In a mouse model of acute neurotoxicity, a single dose of PT-112 was indistinguishable from untreated controls when given at twice the molar concentration of oxali, which induced a significant increase in cold hypersensitivity. After repeat doses over 4 weeks to test for indicators of chronic neuropathy, PT-112 caused minimal accumulation of Pt in dorsal root ganglia (DRG) nerve tissue and no significant loss in nerve conduction velocity (NCV), while oxali treatment caused both dose-dependent declines in NCV and significantly greater Pt accumulation in DRG. Reductions in NCV are indicative of chronic neuropathy and have been shown to be caused by DRG Pt accumulation.

Example 1

PT-112 Induces Immunogenic Cell Death (ICD)

While apoptosis is frequently tolerogenic or nonimmunogenic, certain agents can induce a form of apoptosis in cancer cells called ICD. When cancer cells are killed via exposure to ICD-inducing agents, they release Damage Associated Molecular Patterns (DAMPs). These molecules serve to alert the immune system to the presence of cancer cells via the activation of dendritic cells and, subsequently, cytotoxic T cells. For a comprehensive review, see Kroemer et al., 2013 *Annu. Rev. Immunol.* 31:51-72.

Two such DAMPs are high mobility group box 1 (HMGB1) and calreticulin (CRT). HMGB1 is released from dying cells during ICD, whereas CRT migrates from the endoplasmic reticulum to the cell surface during ICD. To test if PT-112 exposure results in these events that are considered hallmarks of ICD, in vitro experiments using the HCT116 colorectal cancer cell line were conducted. In both cases, oxaliplatin was used as a positive control, as it has been previously been demonstrated to be an ICD-inducing agent.

Figure 1:
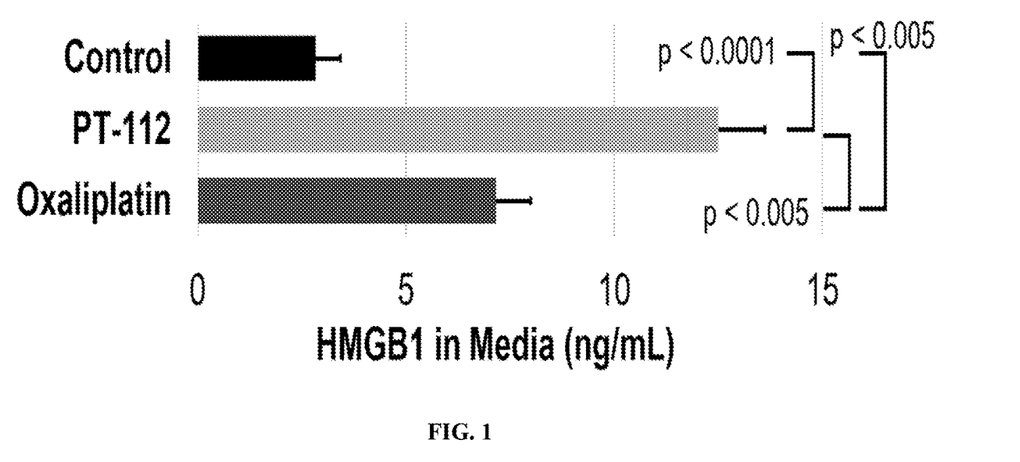
FIG. 1 illustrates the release of high mobility group box 1 (HMGB1) from cells treated with PT-112. HMGB1 in the media of cells after 48 hours of drug treatment was measured via ELISA. HMGB1 release is involved in ICD and antigen presentation to dendritic cells. Error bars indicate 1 SEM, and p values were generated using two-tailed t-tests.

To test for the release of HMGB1, HCT116 cells were treated with $IC_{50}$ concentrations of PT-112 or oxaliplatin for 48 hours. Subsequently, HMGB1 in the media of the cells was measured via ELISA. While the use of oxaliplatin did result in HMGB1 release as indicated by elevated levels of HMGB1 in the media versus untreated control cells, the magnitude of HMGB1 release was significantly higher in the PT-112-treated cells (FIG. 1).

Figure 2:
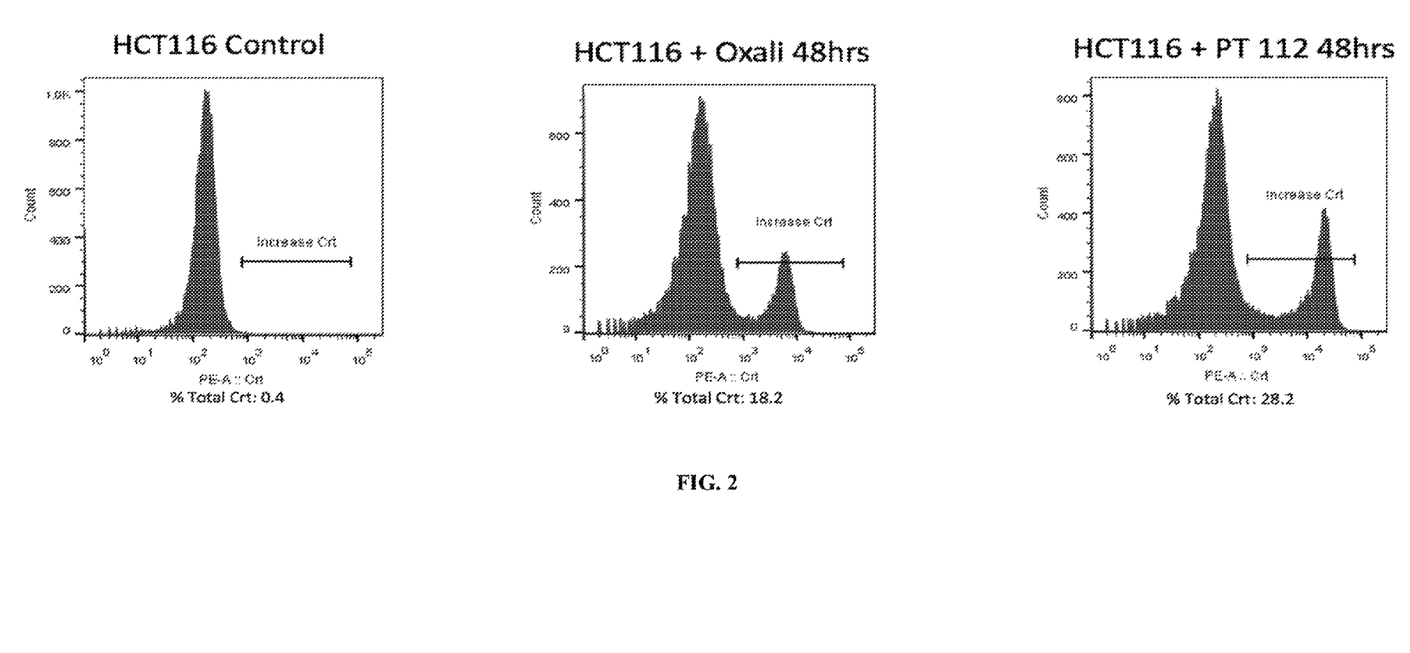
FIG. 2 illustrates the cell surface exposure of calreticulin (CRT) from cells treated with PT-112. CRT cell surface expression was measured via flow cytometry after 48 hours of drug treatment. A peak present to the right of the main peak indicates cells staining positive for CRT, a hallmark of ICD and an indicator of phagocyte targeting.

In a separate experiment, untreated control HCT116 cells were compared to cells exposed to $IC_{50}$ concentrations of oxaliplatin or PT-112 for 48 hours. Cells were then stained with an anti-CRT antibody, and positive staining was detected via flow cytometry. (FIG. 2) Both treatment groups showed enhanced staining relative to control, with a greater effect seen in the PT-112-treated cells.

Both of the above experiments indicate that PT-112 not only shares the ICD-inducing properties of oxaliplatin, but also induces ICD to a greater extent.

Figure 3:
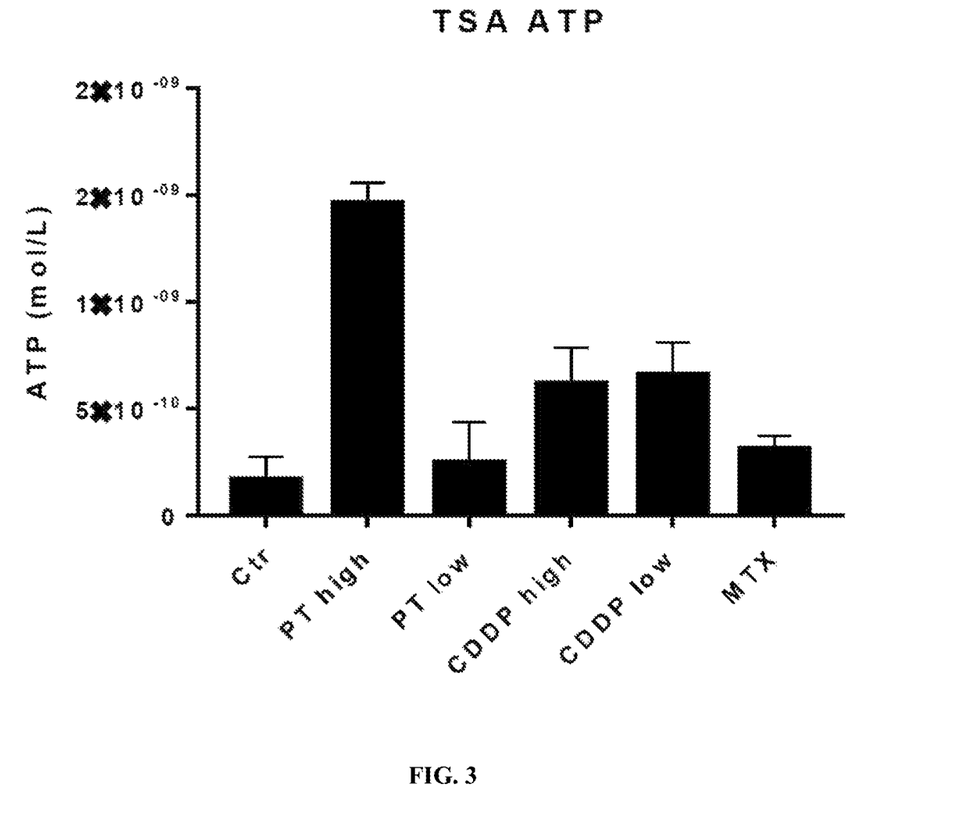
FIG. 3 illustrates the release of adenosine triphosphate (ATP) from cells treated with PT-112. ATP in the media of cells after 48 hours of drug treatment was measured via a luminometric assay. PT-112 was tested in two concentrations, as was cisplatin (a negative control for ICD), in addition to a single concentration of mitoxantrone (a positive ICD control) and an untreated negative control sample. ATP release is indicative of ICD and involved in recruitment and activation of antigen-presenting cells.

PT-112 was also tested for its ability to release the DAMP ATP (FIG. 3), which is involved in the recruitment and activation of antigen-presenting cells. Here, murine TSA cells were exposed to either PT-112 at two different concentrations, cisplatin (a negative control for ICD, also at two concentrations), mitoxantrone (a positive ICD control), or no drug control for 48 hours. Subsequently, ATP in the media was measured via a luminometric assay. The experiment revealed that PT-112 caused robust release of ATP, particularly at the higher concentration. This is again indicative of PT-112 robustly causing ICD.

The "gold standard" for ICD validation is a vaccine experiment, where mice are injected with dead cell material generated by exposing cells to an anticancer agent. Importantly, the anti-cancer agent is removed, and the mice are only injected with the dead and dying cells. Subsequently, after 1-2 weeks, mice are then challenged with an injection of live tumor cells of the same type used to create the vaccine. If the agent used to kill the cells used in the first injection induces ICD, that injection serves as an effective vaccine, and mice do not develop tumors after being challenged with the live tumor cells. If the agent used to create the vaccine kills the cells but does not induce ICD, the vaccine is largely ineffective and mice will subsequently develop tumors.

Figure 4:
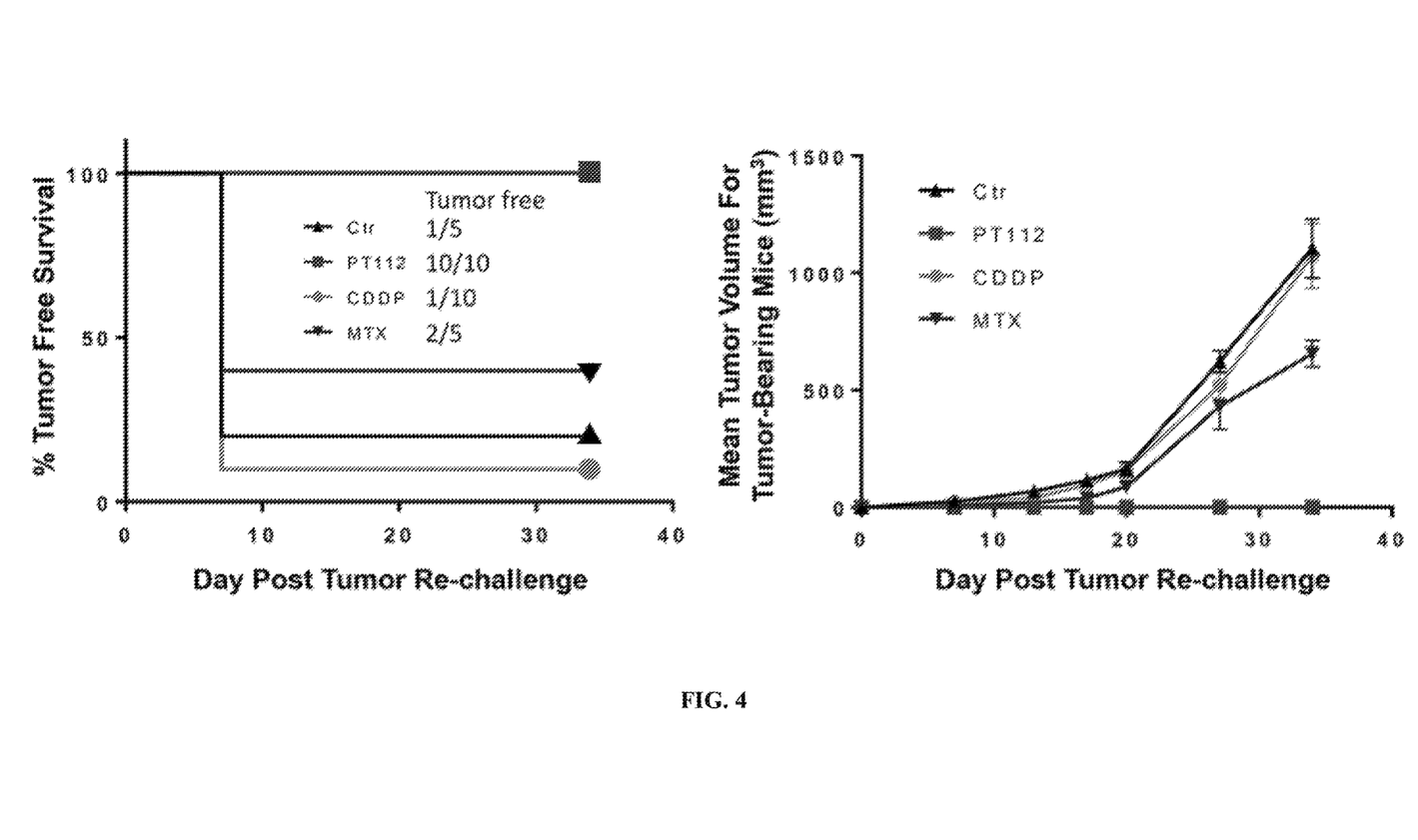
FIG. 4 illustrates the survival advantage conferred when different vaccines are given to mice before being challenged with a live tumor cell injection. Vaccines are composed of dead and dying cancer cells of the same cell line exposed to different anti-cancer agents, killed by exposure to different agents. All (100%) of the mice treated with a PT-112-derived vaccine survived, indicating that PT-112 strongly induces ICD.

This vaccination experiment was conducted using four different treatment groups, one unvaccinated negative control, and three receiving vaccines from the use of different agents: cisplatin (a negative control, non-ICD inducer), mitoxantrone (a positive control ICD inducer), and PT-112 (the experimental arm) (FIG. 4). The vast majority of mice (80-90%) in both negative control groups developed tumors rapidly (within one week). The positive control group vaccine was more effective both in terms of a higher percentage of mice remaining tumor free (40%), and those that were not had slower growing tumors verses those in the negative control groups. In contrast, 100% of mice in the PT-112 vaccine group were tumor free for over one month, again indicating that PT-112 induces ICD, and that it is a particularly potent ICD inducer.

Cancers with low levels of tumor-infiltrating lymphocytes (TILs) tend to be non-responsive to treatment with the emerging class CPIs. CPIs work by disrupting the immunosuppressive interaction between the PD-1 receptor on T-cells and the PD-L1 receptor ligand on tumor cells. In the absence of TILs, there is no interaction to be blocked and checkpoint inhibitors are ineffective. Given that ICD-inducing agents can promote T-cell activation and recruitment into tumors, there is a rationale for the combination of checkpoint inhibitors with ICD-inducing agents and reason to believe that these combinations would be synergistic. Thus, observations of PT-112 significantly enhancing activity of checkpoint inhibitors would be additional evidence of PT-112 being an inducer of ICD.

Example 2

Figure 5:
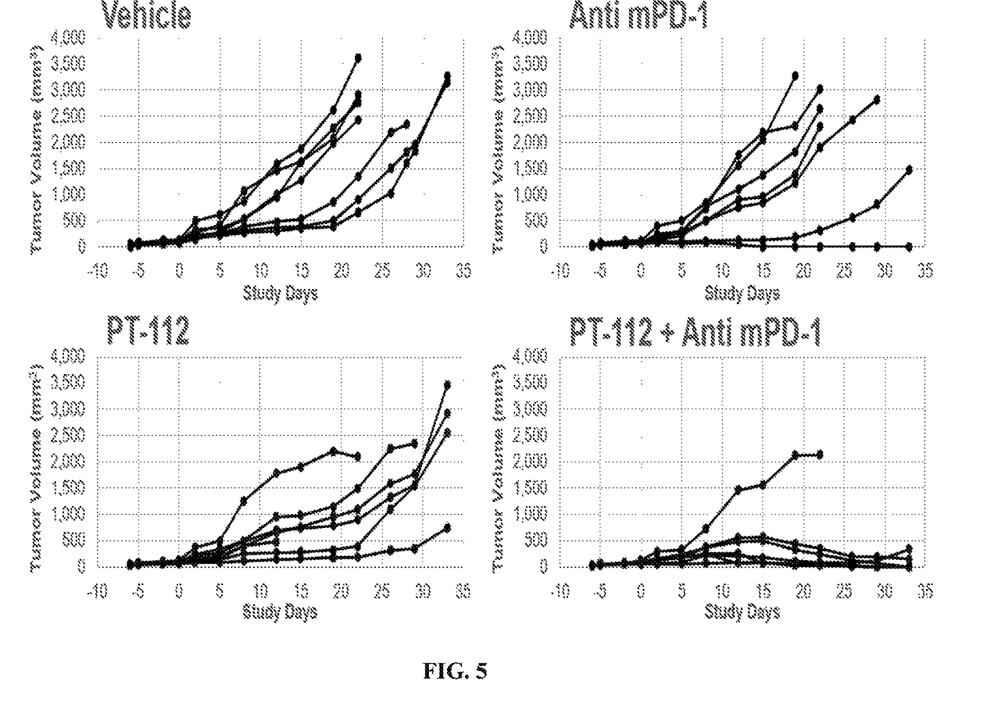
FIG. 5 illustrates a mouse allograft experiment, whereby immune-competent mice were implanted with CT26 mouse colon cancer cells then treated with a vehicle control, PT-112, an anti-PD-1 antibody, or both PT-112 and the antibody. The use of both agents resulted in substantial more anti-tumor activity versus the use of either agent alone. Every dotted line represents the tumor volume of an individual mouse.

Test of PT-112 Immunomodulation, and Synergy in Combination with a PD-1 CPI, in a Mouse Allograft Experiment In a mouse allograft experiment, immuno-competent mice were implanted with CT26 mouse colon cancer cells (FIG. 5). Mice were subsequently randomized into groups (n=7) and treatment was initiated on Day 1 with 90 mg/kg PT-112 IV administered once a week for a total of 6 doses, on Day 2 with 10 mg/kg anti-PD-1 antibody administered twice a week for a total of 6 doses, or the combination of the two. Additionally, control animals were dosed with vehicle. Tumor volumes were monitored during and post treatment.

Results showed that treatment with PT-112 was more effective than treatment with anti-PD-1 antibody alone (54% TGI for PT-112 compared with 19% TGI for anti-PD-1 antibody), but combination therapy with PT-112 and anti-PD-1 antibody was dramatically more effective than either agent alone (83% TGI for the combination of PT-112+ anti-PD-1 antibody). Cures were observed in 1/7 mice treated with the anti-PD-1 antibody alone and in 5/7 mice treated with the combination of PT-112 plus the anti-PD-1 antibody.

The improved control of tumor growth and quintupling of the complete response (cure) rate upon the addition of PT-112 to the anti-PD-1 treatment is supportive of PT-112 inducing ICD.

Figure 6:
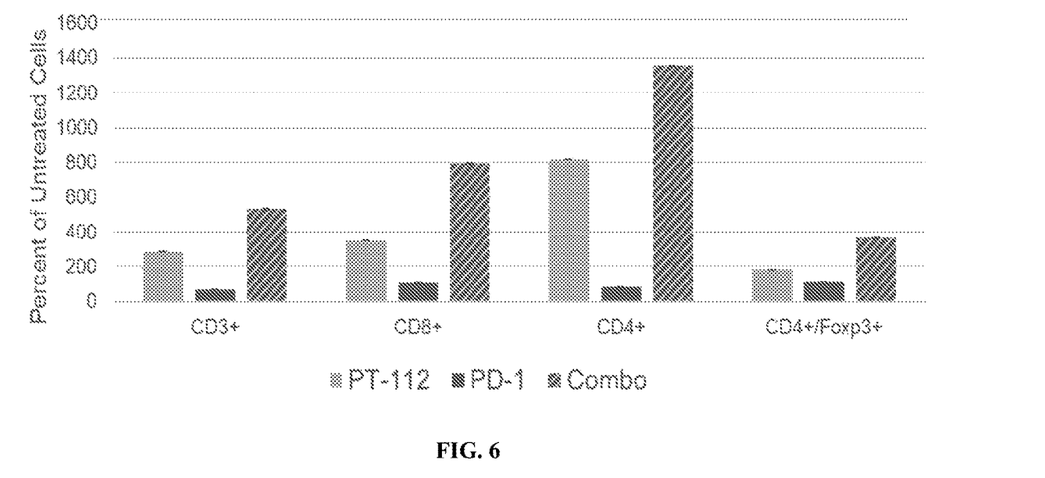
FIG. 6 illustrates fluorescence-activated cell sorting (FACS) analysis of tumor biopsies from a mouse allograft experiment, whereby immune-competent mice were implanted with CT26 cells and were subsequently randomized into control, PT-112, anti-PD-L antibody, or combination treatment. Bars are normalized to the control group. Substantial increases in various T cell populations were observed in PT-112 treatment groups.
Figure 7:
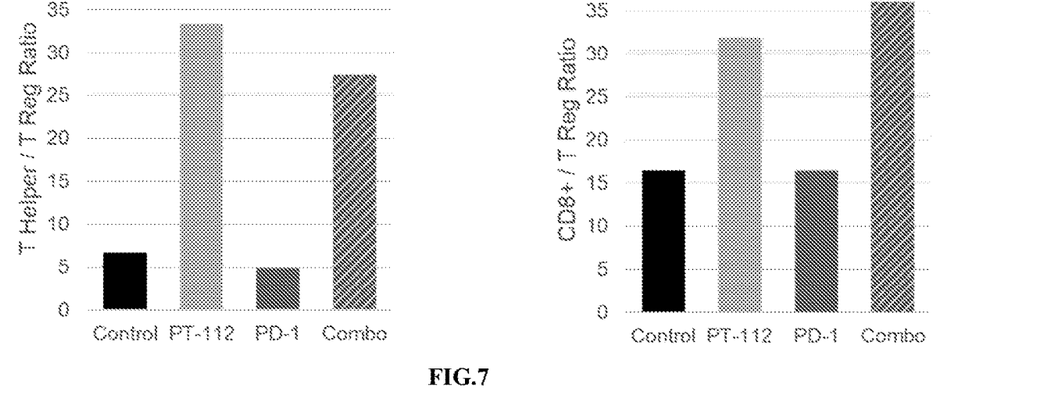
FIG. 7 illustrates the effect of various treatments on the ratios of different cell populations from tumor biopsies in a mouse allograft experiment using the CT26 cell line, where mice were randomized into vehicle control, PT-112, anti-PD-L antibody, and combination treatment groups. PT-112 treatment groups had large increases in the ratio of immunogenic to immunosuppressive cell types, indicating PT-112 induces a more immunogenic tumor microenvironment.

After treatment discontinuation, four of the seven mice from the combination arm were re-challenged with CT26 cell implantation; in all cases, the cells were rejected despite a typical high acceptance rate in untreated animals, indicating an immune memory component to the anti-tumor response is present, consistent with the induction of ICD and synergistic results when used in combination with CPIs. Additionally, tumor tissue was removed from additional treated mice and analyzed via FACS for differences in white blood cell populations. Treatment with the anti-PD-1 antibody did not result in substantial changes in any of the measured cell populations, whereas treatment with PT-112, alone or in combination, caused large changes in cytotoxic T cell (CD8+) and helper T cell (CD4+) populations (FIG. 6), and favorable changes in the ratio of immunogenic to immunosuppressive T cell populations (FIG. 7).

Example 3

Figure 8:
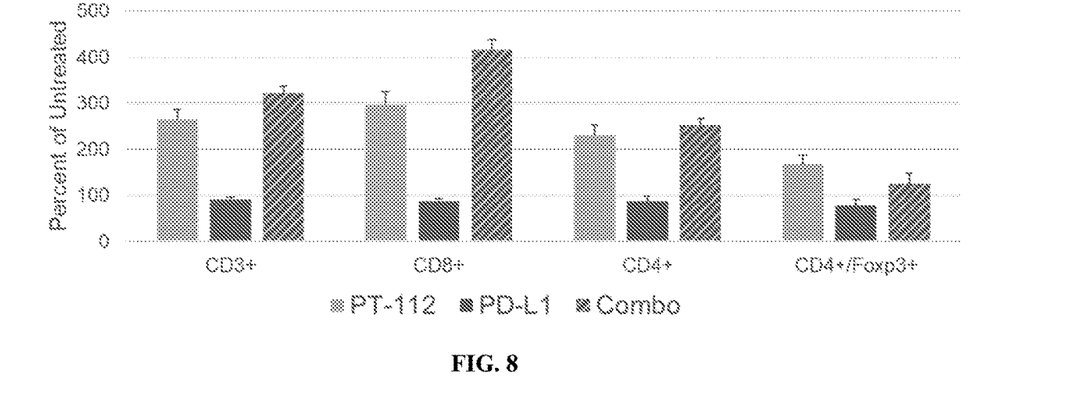
FIG. 8 illustrates fluorescence-activated cell sorting (FACS) analysis of tumor biopsies from a mouse allograft experiment, whereby immune-competent mice were implanted with MC38 cells and were subsequently randomized into control, PT-112, anti-PD-L1 antibody, or combination treatment. Bars are normalized to the control group. Substantial increases in various T cell populations were observed in PT-112 treatment groups.

Test of PT-112 Immunomodulation, and Synergy in Combination with a PD-L1 CPI, in a Further Mouse Allograft Experiment Positive efficacy results using a combination of PT-112 and an anti-PD-L1 antibody in the MC38 murine cancer model were observed, similar to those described in Example 2 (data not shown). To better understand the effects of the different treatments on T cell populations, additional immuno-competent mice were implanted with MC38 cells and were subsequently randomized into control, PT-112, anti-PD-L1 antibody, or combination treatment arms (n=5). After 2 weeks of treatment (PT-112 @ 90 mg/kg QW and PD-L1 @ 10 mg/kg BIW), tumor tissue was removed and analyzed via FACS for differences in white blood cell populations. Treatment with the anti-PD-L1 antibody did not result in substantial changes in any of the measured cell populations, whereas treatment with PT-112 caused large changes in various cell populations, including cytotoxic T cells (CD8+) and helper T cells (CD4+) (FIG. 8). These changes were even more pronounced in the combination arm. Note that data are normalized to samples collected from untreated mice, which are defined as 100%.

Figure 9:
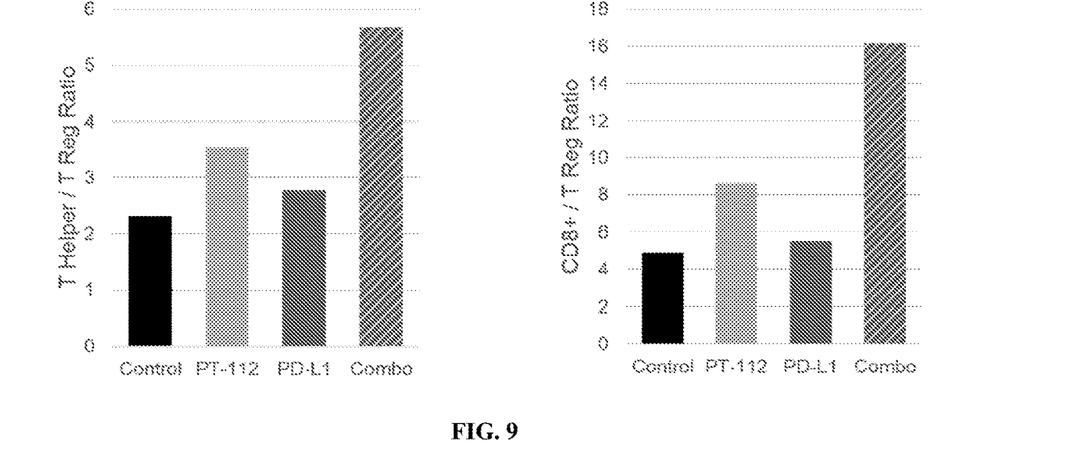
FIG. 9 illustrates the effect of various treatments on the ratios of different cell populations from tumor biopsies in a mouse allograft experiment using the MC38 cell line, where mice were randomized into vehicle control, PT-112, anti-PD-L1 antibody, and combination treatment groups. PT-112 treatment groups had large increases in the ratio of immunogenic to immunosuppressive cell types, indicating PT-112 induces a more immunogenic tumor microenvironment.

Not all white blood cell populations are immunogenic. Some populations, such as regulatory T (CD4+/FoxP3+) cells are immunosuppressive. To better understand if the changes observed would have a net immunogenic or immunosuppressive effect, ratios of different cell populations were calculated (FIG. 9). While the anti-PD-L1 treatment didn't affect these ratios, treatment with PT-112 or the combination of the two had positive effects on both the ratios of helper T cells to regulatory T cells and the ratios of cytotoxic T cells to regulatory T cells, with the greatest effects coming from the combination treatment.

These results are again consistent with the hypothesis that PT-112 induces ICD, may explain the potent synergy observed in the previously described allograft experiment using the CT26 mouse model and support the use of PT-112 in conjunction with CPIs.

Example 4

Figure 10:
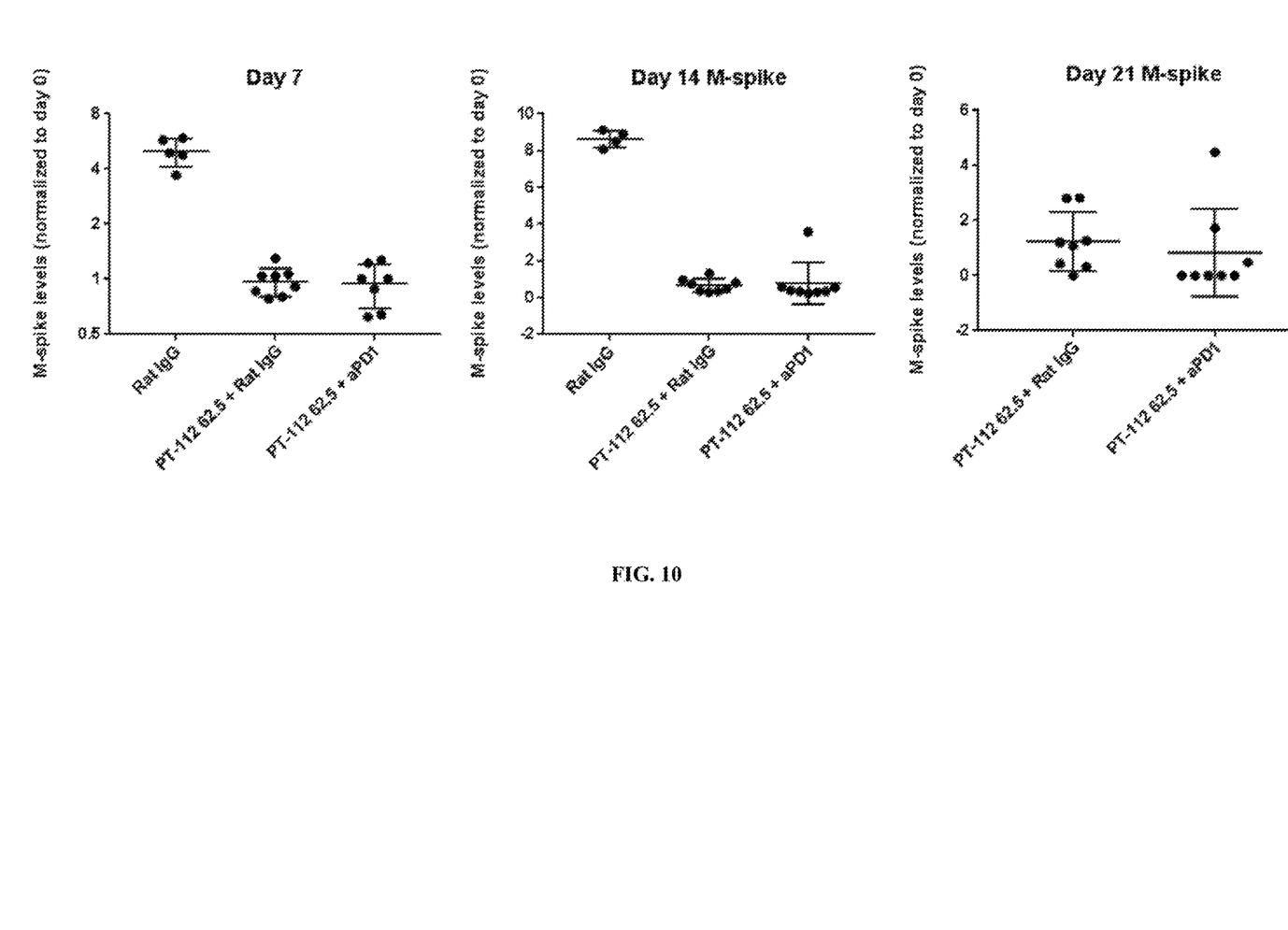
FIG. 10 illustrates the use of PT-112 alone or in combination with an anti-PD-1 antibody in mice implanted with the bortezomib-resistant multiple myeloma cancer model vk12598. This model is also resistant to monotherapy anti-PD-1 treatment. The use of PT-112 alone or in combination resulted in large drops in M-spike, indicative of responses. The responses were deeper in the combination arm.

Test of PT-112 Potency and Synergy with CPI in an Immune-Competent Multiple Myeloma Mouse Model In a different experiment, the use of PT-112 was tested in mice implanted with the bortezomib-resistant multiple myeloma cancer model vk12598, described in Chesi et al. 2012. The M-spike levels of mice in the sham antibody (Rat IgG) control group (n=5), PT-112+ sham antibody group (n=8), or PT-112+ anti-PD-1 antibody group (n=8) were measured as a means to monitor disease progression (FIG. 10).

Control mice showed rapid increases in M-spike levels, and all of these mice died by 21 days post-treatment start. PT-112-containing groups had decreases in M-spike levels over time, with several complete responses observed after 21 days post-treatment start. Notably, all of the PT-112 treated mice survived to this time point. Despite the fact that treatment with the anti-PD-1 antibody alone showed no significant efficacy in this model in separate experiments, the number of complete responses (defined as M-spike=0) was higher in the PT-112+ anti-PD-1 combination arm versus the PT-112+ sham antibody arm.

The observed activity of the anti-PD-1 antibody only when used in conjunction with PT-112 is again supportive of that PT-112 is an ICD-inducing agent.

PT-112 bears the hallmarks of a highly differentiated, pleiotropic and well-tolerated anti-cancer agent. Specifically, PT-112: (1) works effectively in both in vitro and in vivo cancer models; (2) is minimally impacted by DNA repair pathways, suggesting DNA is not the primary target; (3) acts in part through the p53/MDM2 pathway, along with G1/S cell cycle regulators; (4) induces the hallmarks of ICD; (5) is stable in plasma; (6) results in negligible renal toxicity relative to cis at significantly higher doses; and (7) produces no measurable signs of acute or chronic neuropathy in contrast to oxali. Additionally, the concentrations used herein relate to PT-112 plasma levels achievable in human patients at sub-toxic doses. These findings suggest that PT-112 represents a clinically relevant departure from the paradigm associated with approved Pt agents.

The foregoing non-limiting examples and embodiments are described to illustrate certain aspects of the present invention. Those skilled in the art will understand that various changes or modifications may be made without departing from the spirit and scope of the invention. All references mentioned herein are incorporated by reference in their entirety.

What is claimed is:

1. A method for treating a subject having cancer, comprising administering to the subject a therapeutically effective amount of a phosphaplatin compound having a structure of formula I or II:

or a pharmaceutically acceptable salt thereof, to induce immunogenic cell death (ICD) in the subject, and a therapeutically effective amount of an immune checkpoint protein inhibitor, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

2. The method of claim 1, wherein $R^1$ and $R^2$ are each independently selected from $NH_3$, methyl amine, ethyl amine, propyl amine, isopropyl amine, butyl amine, cyclohexane amine, aniline, pyridine, and substituted pyridine; and $R^3$ is selected from 1,2-ethylenediamine and cyclohexane-1,2-diamine.

3. The method of claim 1, wherein the phosphaplatin compound is selected from the group consisting of:

pharmaceutically acceptable salts, and mixtures thereof.

4. The method of claim 1, wherein the phosphaplatin compound is R,R-pyrodach-2:

5. A method for treating a subject having cancer, comprising administering to the subject a therapeutically effective amount of a phosphaplatin compound having a structure of formula III or IV:

or a pharmaceutically acceptable salt thereof, to induce immunogenic cell death (ICD) in the subject, and a therapeutically effective amount of an immune checkpoint protein inhibitor, wherein $R^1$ and $R^2$ are each independently selected from $NH_3$, substituted or unsubstituted aliphatic amines, and substituted or unsubstituted aromatic amines; and wherein $R^3$ is selected from substituted or unsubstituted aliphatic diamines, and substituted or unsubstituted aromatic diamines.

6. The method of claim 5, wherein $R^1$ and $R^2$ are each independently selected from $NH_3$, methyl amine, ethyl amine, propyl amine, isopropyl amine, butyl amine, cyclohexylamine, aniline, pyridine, and substituted pyridine; and $R^3$ is selected from 1,2-ethylenediamine and cyclohexane-1,2-diamine.

7. The method of claim 5, wherein the monomeric platinum (IV) pyrophosphate complex has a formula (IV), wherein $R^3$ is 1,2-ethylene-diamine or cyclohexane-1,2-diamine.

8. The method of claim 1, wherein the administering comprises intravenous or intraperitoneal injection.

9. The method of claim 1, wherein the dose of pyrophosphate platinum complex is in the range of from about 1 mg and to about 200 mg/Kg based on body weight of the subject.

10. The method of claim 1, wherein the cancer is selected from the group consisting of colon cancer, pancreatic cancer, gastric cancer, liver cancer, breast cancer, prostate cancer, lung cancer, and melanoma, osteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JIVIML), myelodysplastic syndromes, myelofibrosis, myeloproliferative neoplasms, polycythaemia vera, thrombocythaemiaosteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma and leukemia.

11. The method of claim 1, in conjunction with administering to the subject an additional anti-cancer agent.

12. The method of claim 11, wherein the additional anti-cancer agent is selected from the group consisting of alkylating agents, glucocorticoids, immunomodulatory drugs (IMiDs) and proteasome inhibitors, cyclocreatine, a RNAi agent, a nucleic acid, a vector, 5-fluorouracil, Oxaliplatin, Irinotecan, Capecitabine, Gemcitabine, Cetuximab, Paclitaxel, Bevacizumab, folinic acid (leucovorin), Regorafenib, Aflibercept, topoisomerase I inhibitors, NKTR-102, Tivantinib, PX-866, Sorafenib, Linifanib, kinase inhibitors, Telatinib, XL281 (BMS), Robatumumab, and IGF1-R Inhibitors.

13. The method of claim 3, wherein the phosphaplatin compound is administered to the subject prior to administration of the immune checkpoint protein inhibitor or at the same time as administration of the immune checkpoint protein inhibitor.

14. The method of claim 3, wherein the subject is a patient having a cancer having low or no response to treatment with an immune checkpoint protein inhibitor alone.

15. The method of claim 3, wherein the immune checkpoint protein inhibitor is selected from the group consisting of PD-1 inhibitors, PD-L1 inhibitors, B7-1/B7-2 inhibitors, CTLA-4 inhibitors, and combinations thereof.

16. The method of claim 3, wherein the immune checkpoint protein inhibitor is an antibody selected from the group consisting of Pembrolizumab, Nivolumab, Pidilizumab (CT-011), Atezolizumab, Avelumab, Durvalumab, Ipilimumab, and combinations thereof.

17. The method of claim 3, wherein the cancer is selected from the group consisting of colon cancer, pancreatic cancer, gastric cancer, liver cancer, breast cancer, prostate cancer, lung cancer, bladder cancer, urothelial carcinoma, thymic epithelial tumors, head and neck cancer, skin cancers, osteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma, leukemia, childhood acute myelogenous leukemia (AML), chronic myelomonocytic leukaemia (CMML), hairy cell leukaemia, juvenile myelomonocytic leukaemia (JIVIML), myelodysplastic syndromes, myelofibrosis, myeloproliferative neoplasms, polycythaemia vera, thrombocythaemiaosteosarcoma, chondrosarcoma, Ewing tumor, malignant fibrous histiocytoma (MFH), mibrosarcoma, giant cell tumor, chordoma, spindle cell sarcomas, multiple myeloma, non-Hodgkin lymphoma, Hodgkin lymphoma and leukemia.

18. The method of claim 3, wherein the cancer is characterized with a low level of tumor-infiltrating lymphocytes (TILs).

19. The method of claim 1, wherein induction of the immunogenic cell death by the phosphaplatin compound is characterized by release of damage associated molecular patterns (DAMPs), high mobility group box 1 (HMGB1), calreticulin (CRT), and DAMP adenosine triphosphate (ATP) from cells of the subject treated with the phosphaplatin compound.

* * * * *